United States Patent [19]

Horan et al.

[11] Patent Number: 4,762,701
[45] Date of Patent: Aug. 9, 1988

[54] IN VIVO CELLULAR TRACKING

[75] Inventors: Paul K. Horan, West Chester; Sue E. Slezak, Downingtown, both of Pa.

[73] Assignee: SmithKline Beckman Corporation, Philadelphia, Pa.

[21] Appl. No.: 925,445

[22] Filed: Oct. 31, 1986

[51] Int. Cl.$^4$ .................. A61K 49/02; A61K 49/00
[52] U.S. Cl. ..................................... 424/1.1; 424/9; 514/824
[58] Field of Search ............... 514/824, 825, 866, 903; 424/1.1, 9

[56] References Cited

U.S. PATENT DOCUMENTS

| | | | |
|---|---|---|---|
| 3,673,410 | 6/1972 | Waite et al. | 424/1.1 X |
| 4,343,782 | 8/1982 | Shapiro | 424/3 |
| 4,401,647 | 8/1983 | Krohn et al. | 424/1.1 |
| 4,424,201 | 1/1984 | Valinsky et al. | 424/3 |
| 4,478,815 | 10/1984 | Burchiel et al. | 424/1.1 |

OTHER PUBLICATIONS

Fox, I. J. et al., *Proc. Mayo Clinic,* 32:478–484 (1957).
Schad, H. et al., *Pfluegers Arch. Eur. J. Physiol.,* 370(2):139–144 (1977).
Wanda, P. E. and Smith, J. D., *J. Histochem. Cytochem.,* 30:1297–1300 (1982).
Axelrod, D., *Biophysical J.,* 26:557–574 (1979).
Honig, M. G. and Hume, R. I., *J. Cell Biology,* 103:171–187 (1986).
Johansson, L. B. A. et al., J. Chem. Soc., Faraday Trans. 1:81(6): 1389–1400 (1985).

*Primary Examiner*—John F. Terapane
*Assistant Examiner*—John S. Maples
*Attorney, Agent, or Firm*—Vincent L. Fabiano; Stuart R. Suter; Alan D. Lourie

[57] ABSTRACT

Methods of tracking cells in vivo and for determining in vivo cell lifetimes. Cells are labelled with cyanine dyes and detection is by measuring fluorescence, absorbance, or by detecting nuclear magnetic resonance probes included in the cyanine dyes. Using the invented methods, for example, red blood cell and platelet lifetimes are determined. Also, cells are tracked to determine sites of primary or metastatic tumors, or sites of occult infection. Further, rates at which cells pass through vessels is used to determine blood vessel patency and platelet aggregation.

40 Claims, No Drawings

IN VIVO CELLULAR TRACKING

BACKGROUND OF THE INVENTION

1. Field of the Invention

This invention relates to methods of tracking cells in vivo and methods for determining in vivo cell lifetime.

2. Background Information

In vivo cellular tracking and lifetime determination require that cells be labelled with a marker that is stable in the cell, i.e., is not lost from the cell, and that does not significantly affect cell function. Presently available markers fail to provide the necessary characteristics. Fluorescent antibodies, for example, are not suitable because they readily dissociate from the cells. Other potential markers cannot be used because they interfere with cell function.

Cyanine dyes have been used in various biological applications. Dioxacarbocyanine dyes have been used in performing white blood cell differential counts. Gunter Valet, Max planck Ges Wissensch; Patent Accession Number 84-102307/17, *Simultaneous Quantitative Determination of Blood Cells by Selective Staining and Measuring Volume and Fluorescence*. The dyes utilized in these studies, however, are short chain carbocyanine dyes (less than ten carbons) and respond to changes in membrane potentials. Furthermore, the short chain carbocyanine dyes enter the cells mitochondria, are cytotoxic, and when the cells are washed these dyes easily leak out of the cell whether or not the membrane potential of the cell is changed. Other short aliphatic chain cyanine dyes are used in many other biological assays. The short chain molecules, however, respond to membrane potentials and cross the cell membrane, penetrating into the mitochondria. H. M. Shapiro, U.S. Pat. No. 4,343,782, Aug. 10, 1982. The short chain dyes also are toxic to cells and cannot be used to track cells in vivo.

Tricarbocyanine dYes (Fox, I. J., et al., *Proc. Mayo Clinic,* 32:478-484, 1957 ) and Evans-Blue dye (Schad, H., et al., *Pfluegers Arch. Eur. J. Physiol.,* 370(2):139-144, 1977) have been used in vivo to estimate cardiac output by a dilution method. Dow (Dow, P., *Physiol. Rev.,* 36:77-102, 1956) describes the method as injection of a known amount of some intravascular indicator on the venus side of the lungs, and measurement of the time course of arterial concentration of the indicator to determine the volume between the points of injection and sampling. These dyes are not used to stain cells.

SUMMARY OF THE INVENTION

Presently invented are novel procedures for tracking cells in vivo and for determining in vivo cell lifetime. According to the presently invented novel cell tracking procedures, the cells first are labelled with a cyanine dye and then are injected into a subject and the cyanine dye is used to locate the cells. In another embodiment, cell lifetime is determined by measuring the rate of disappearance of labelled cells.

DETAILED DESCRIPTION OF THE INVENTION

In the presently invented methods for tracking cells in vivo and for determining in vivo cell lifetimes, the cells are labelled with cyanine dyes. Compounds having the following structure are referred to herein as cyanine dyes:

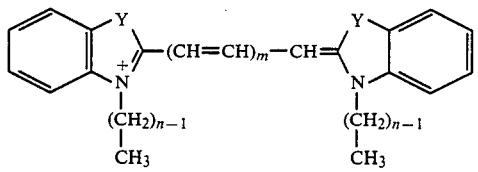

in which:

Y is oxygen, sulfur, methylene or alkylsubstituted methylene;

m is 0-3; and n is 12-22.

As used herein, alkyl-substituted methylene refers to mono- or di- substituted methylene having any combination of methyl, ethyl, or propyl substituents.

Compounds of the above structure are referred to by the following generally understood shorthand formula:

$$DiYC_n(2m+1)$$

Sims, P. J., et al., *Biochem,* 13:3315 (1974). Thus, for example, the compound wherein Y is sulfur and having three carbons bridging the rings and two fourteen carbon aliphatic chains is referred to as $DiSC_{14}(3)$. Similarly, $DiIC_{14}(5)$ indicates the compound wherein Y is isopropyl, and having five carbons bridging the rings and two fourteen carbon aliphatic chains.

Included within compounds referred to herein as cyanine dyes are compounds of the above structure having one or more substitutions provided such substituted compounds are soluble in cell labelling media for at least as long as needed for labelling and have a sufficiently high membrane partition coefficient to remain associated with labelled cell membranes. Such compounds also must not significantly affect cell viability in the concentrations required for labelling. Solubility in cell labelling media is determined as shown below by dispursing a cyanine dye in the labelling media and, by standard spectrafluorometric techniques, measuring fluorescence intensity over time. Decreasing fluorescence intensity indicates dye precipitation and adherence to vessel walls. Whether the dyes remain associated with cell membranes is determined, for example, using known flow cytometric procedures to monitor fluorescence intensity of red blood cells injected into the donor animal after labelling. Essentially constant fluorescence intensity of the labelled cells after injection establishes stability of the dye in cell membranes.

Also included within compounds referred to herein as cyanine dyes are compounds of the above structure incorporating an atom which can be detected by magnetic reasonance imaging. Such compounds are prepared using known techniques, for example, by incorporating a fluorine atom into one of the methyl groups of the aliphatic chains. Compounds of the above structure tagged with a gamma emitter such as $^{125}I$ also are referred to herein as cyanine dyes.

Cyanine dyes used in the present invention can be purchased from various sources such as Molecular Probes, Inc., Eugene, Oregon, and can be prepared from available starting materials using known synthetic methods. Hamer, F. M., *The Cyanine Dyes and Related Compounds,* Interscience Publishers (1964).

Using the invented procedures any viable cell can be labelled with cyanine dyes. As used herein, the term cell includes nucleated eukaryotic cells such as white blood cells, various tumor cells, other mammalian cells (for example, tissue cultured chinese hamster ovary cells), yeast; and non-nucleated cells such as red blood cells and platelets. A nucleated cell is viable if it is able to grow or function essentially as expected for cells of its type; a non-nucleated cell is viable if it is able to perform its expected functions, for example a viable red cell is able to transport oxygen and carbon dioxide; and viable platelets perform essentially as expected in, for example, aggregation and release assays.

Cell labelling is performed in a medium that is non-lethal to cells and that provides for reproducible cell labelling. To give the medium the necessary characteristics, osmolarity regulating agents in which cyanine dyes form stable solutions for at least as long as required for labelling are used. Acceptable osmolarity regulating agents include agents such as sugars, for example monosaccharides such as glucose, fructose, sorbose, xylose, ribose, and disaccharides such as sucrose, sugar-alcohols, such as mannitol, glycerol, inositol, xylitol, and adonitol, amino acids such as glvcine and arginine, and certain Good's buffers such as N-tris(hydroxvmethyl)-methyl-3-aminopropanesulfonic acid. Good, N. E., et al., *Biochem.* 15, 467–477 (1966), Good, N. E. and S. Izawa, *Methods Enzymol.*, 24, Part B, 53 (1968), Feguson, W. J., et al., *Anal. Biochem.* 104:301-310 (1980). Some cell lines, however, may be sensitive to one or more of the osmolarity regulating agents, especially sugar-alcohols. Thus, prior to labelling, standard tests are conducted to make certain that the cells are viable in the intended osmolarity regulating agent. Additionally, small amounts of buffering agents may be added to the labelling medium to regulate hydrogen ion concentration.

The effect on cell viability of exposure to a variety of osmolarity regulating agents was determined by measuring the doubling time of Yac cells after the cells were exposed for thirty minutes to a variety of osmolarity regulating agents. Yac cells are a mouse lymphoma tissue culture cell line available from the American Type Culture Collection, Rockville, Maryland, and are described in the *European Journal of Immunology* 5:112-117 (1975). As the data shown in Table 1 demonstrate, when compared to phosphate buffered saline, exposure to sucrose, glucose, and the Good's buffers: TAPS, CAPS, EPPS, HEPPSO, and DIPSO resulted in negligible effects on cell doubling time which indicates the absence of exposure-related cellular toxicity.

TABLE I

| Osmolarity Regulating Agent | Doubling Time (Hours) |
|---|---|
| Phosphate Buffered Saline | 31.0 |
| Sucrose | 41.0 |
| Glucose | 34.5 |
| TAPS | 32.7 |
| CAPS | 45.8 |
| EPPS | 32.2 |
| HEPPSO | 23.4 |
| DIPSO | 36.7 |
| 3-Amino-1-propanesulfonic acid | 99.6 |
| Sodium 3-(N—morpholino)propanesulfonic acid (MOPS) | A |
| 2-Amino-2-methyl-1,3-propanediol | B |
| 2-Amino-2-methyl-1-propanol | B |
| N—tris(hydroxymethyl)methylaminoethane-sulfonic acid (TES) | B |
| N,N—bis(2-hydroxyethyl)-2-aminoethane-sulfonic acid (BES) | A |
| 3-(Cyclohexylamino)-2-hydroxy-1-propane-sulfonic acid (CAPSO) | A |
| Triethanolamine | B |

TABLE I-continued

| Osmolarity Regulating Agent | Doubling Time (Hours) |
|---|---|
| Tris(hydroxymethyl)aminomethane (TRIZMA) | B |
| Bis-tris propane | B |
| 2-(N—morpholino)ethanesulfonic acid (MES) | B |
| 3-[Dimethyl(hydroxymethyl)methylamino]-2-hydroxypropanesulfonic acid (AMPSO) | A |
| N,N—bis(2-hydroxyethyl)glycine (BICINE) | 57.7 |
| 3-[(-3-Cholamidopropyl)dimethylammonio]-1-propanesulfonate (CHAPS) | B |
| 3-[N—tris(hydroxymethyl)methylamino]-2-hydroxypropanesulfonic acid (TAPSO) | 63.6 |
| 3-(N—morpholino)-2-hydroxypropane-sulfonic acid (MOPSO) | 178.4 |
| 2-[(2-Amino-2-oxoethyl)amino]ethane sulfonic acid (ACES) | 1038.4 |
| Bis(2-hydroxyethyl)imino-tris-(hydroxymethyl)methane (BIS-TRIS) | A |
| 2-(N—cyclohexylamino)ethane sulfonic acid (CHES) | 51.5 |
| N—tris-(hydroxymethyl)methylglycine (TRICINE) | A |
| Glucosamine | 288.4 |
| Imidazole | B |
| Glycylglycine | 66.9 |

A - No growth or partially cytotoxic
B - Acutely cytotoxic

Table II shows various osmolarity regulating agents that were examined for cyanine dye solubility. All measurements of concentration were made after removal of precipitates by centrifugation and dissolving small aliquots of osmolarity regulating agents containing cyanine dyes into ethanol for spectrofluorometric analysis. The dyes used were $DiSC_{14}(5)$ and $DiOC_{14}(3)$, and the osmolarity regulating agents were at iso-osmotic concentrations. Reductions in fluorescence intensity from the ethanol solution standard directly correlate with reductions in cyanine dye solubility.

| Osmolarity Regulating Agent | Relative Fluorescence Intensity (CONC) | |
|---|---|---|
| | $DiSC_{14}(5)$ | $DiOC_{14}(3)$ |
| Ethanol | 100 | 100 |
| Glucose | 31 | 100 |
| Fructose | 35 | 100 |
| Sorbose | 40 | 100 |
| Sucrose | 41 | 100 |
| Xylose | 36 | 19–52 |
| Ribose | 24 | 100 |
| Lyxose | 0.12 | 1.8 |
| Glycine | 31 | 93 |
| Arginine | 17 | 17.2 |
| Glycerol | 39 | 99.5 |
| Inositol | 42 | 92 |
| Xylitol | 34 | 76.4 |
| Mannitol | 29 | * |
| Adonitol | 34 | ND |
| Tris(hydroxymethyl)-methylaminopropane sulfonic acid (TAPS) | 18 | ND |
| 3-(Cyclohexylamino)-1-propanesulfonic acid (CAPS) | 40 | ND |
| N—(2-Hydroxyethyl)piperazine-N'—3-propanesulfonic acid (EPPS) | 18 | ND |
| N—2-hydroxyethylpiperazine-N'—2-hydroxypropane-sulfonic acid (HEPPSO) | 20 | ND |
| 3-[N—N—bis(2-hydroxyethyl)amino]-2-hydroxypropane-sulfonic acid (DIPSO) | 43*** | ND |
| NaCl | 6 | 1.7 |
| Phosphate Buffered Saline | 2.1 | 6.5 |
| $Na_2SO_4$ | 7.4 | 1.6 |
| NaI | 1.1 | 0.14 |

| | Relative Fluorescence Intensity (CONC) | |
|---|---|---|
| Osmolarity Regulating Agent | $DiSC_{14}(5)$ | $DiOC_{14}(3)$ |
| Choline Chloride | 11** | 6.3 |
| Choline Iodide | 0.16 | 2.3 |

*Precipitate in ethanol, no data obtainable.
**Artifact due to large crystals that did not pellet.
***Precipitate in ethanol (data questionable).
ND Not Determined As can be seen from Table II, cyanine dyes are much less soluble in the presence of classical salts than in the presence of sugars, except lyxose, sugar-alcohols, amino acids, and the Good's buffers, TAPS, HEPPSO, DIPSO, CAPS, and EPPS. Additionally, stability of $DiSC_{14}(5)$ solutions in sugars such as glucose, fructose, ribose, sorbose, sucrose, and xylose, sugar-alcohols such as glycerol, inositol, xylitol, and adonitol, and amino acids such as glycine and arginine was determined. The cyanine dye was stable in the tested solutions for at least twenty minutes, which is sufficient time for reproducible labelling, and in many of the agents the amount of cyanine dye in solution had not significantly decreased at sixty minutes.

Further, the solubility of cyanine dyes in a medium containing classical salts and osmolarity regulators in which the dyes are soluble was evaluated. The solubility of $DiSC_{14}(5)$ in iso-osmotic glucose solution was not significantly affected by dilution with distilled water. $DiSC_{14}(5)$ solubility in iso-osmotic glucose solution, however, was reduced significantly by dilution with only approximately 20% iso-osmotic sodium chloride solution. Thus, reproducible cell labelling with cyanine dyes can be performed in media containing no more than small amounts of classical salts, such as sodium chloride, potassium chloride, calcium chloride, sodium acetate, potassium acetate, sodium sulfate, sodium iodide, choline chloride, or choline iodide, and preferably is performed in a medium in which no classical salts are used to regulate osmolarity.

Cells cyanine dye labelled using the presently invented procedure were analyzed to determine the effect of labelling on cell viability. V79 cells which are available from the American Type Culture Collection, Rockville, Maryland, and are described in Prescott, D. M., *Ann. New York Acad. Sci.*, 397:101-109 (1982), were labelled with a solution containing $DiOC_{14}(3)$ at a concentration of $10^{-5}$ or $4 \times 10^{-5}M$ and the growth kinetics of the stained cells were compared to unstained cells and an equal mixture of stained and unstained cells. Cell doubling time was unaffected by cyanine dye labelling. Thus, labelling had no effect on cell growth. Also, several other standard tests of cell viability such as Trypan Blue Exclusion and Propidium Iodide exclusion confirmed an absence of effect on cell viability of cyanine dye labelling according to the described procedures.

The effect of cyanine dye labelling on cell viability also was determined by measuring red cell fragility. Labelled and unlabelled red blood cells were suspended in sodium chloride media of various osmotic strengths by varying the salt concentration. Volume distributions of the cells were measured using a Coulter Counter ® with a channelizer attachment. Mean volumes were determined and plotted for each salt concentration, and volumes were increased as the sodium chloride concentration decreased until approximately 0.5 grams/100 ml where the volume displays a precipitous drop. At this point, the red cells lyse. Furthermore, the volume changes were the same whether or not the cells were labelled with a cyanine dye. In a simlar fashion, hemolysis was monitored in parallel samples as a function of sodium chloride concentration. After the red cells were placed into sodium chloride for approximately 2-3 minutes, the solutions were centrifuged to pellet any unlysed cells. Supernatant solutions then were subjected to spectrophotometric analysis to determine the hemoglobin concentrations. Percent lysis was determined by comparing hemoglobin concentrations of each sample to a totally lysed control. Free hemoglobin concentration was relatively low until approximately 0.5 grams sodium chloride/100 ml was reached, and then hemoglobin was released immediately. By comparison with the red cell fragility results, the volume changes were directly correlated to the release of hemoglobin. Furthermore, the release of hemoglobin was the same in labelled and unlabelled cells.

To test in vivo stability of cells cyanine dye labelled according to the presently invented method, rabbit red cells were withdrawn, labelled with $DiSC_{14}(5)$, and reinfused. Periodically thereafter, blood samples were obtained and analyzed for percent labelled cells and fluorescence intensity of the labelled cells. The number of circulating red cells decreased linearly as a function of time and the measured 52 day lifetime of labelled cells correlated closely with the 40 to 60 day average reported life time of rabbit red cells. Thus, cyanine dye labelling did not affect the clearance rate of red blood cells.

In all but one of the five rabbits tested, fluorescence intensity of the stained cells remained essentially unchanged 60 days after labelling and reinjection. In the fifth animal, not more than 20% of the cyanine dye had migrated from the labelled cells after 60 days in the rabbits' circulation. These data combined with data from tissue culture showing no transfer of dye from labelled to unlabelled cells demonstrates that the cells are stably labelled with the dyes.

Viable cells labelled with cyanine dyes are used in the presently invented in vivo cellular tracking and in vivo cell lifetime analyses in mammalian subjects, including humans. As used herein in vivo cellular tracking includes determining location of cells in the subject's body and measuring the rate at which cells pass a certain point, for example, the rate at which cells flow through a blood vessel.

The lifetime of transfused red blood cells is determined by including in the transfusion an aliquot of cyanine dye-labelled red blood cells. Immediately after transfusion, using standard techniques a determination of the fraction of labelled red blood cells in the systemic circulation is made. Subsequent determinations of percent labelled cells are used to calculate lifetime of the transfused cells. Further, post transfusion bleeding is distinguished from immunologic reaction by comparing changes in the fraction of labelled cells to changes in the hematocrit. Equivalent rates of reductions in pneumatic and percent labelled cells indicates blood loss caused by bleeding, whereas comparatively higher rates of reduction of labelled cell counts indicates an immunologic reaction to the transfused cells. To avoid autofluorescence and self-quenching by hemoglobin, red cells preferably are labelled with a cyanine dye which is excited within the red wavelengths and emits further to the red than the excitation wave lengths of hemoglobin. Examples of such dyes include $DiC_{14}(5)$ and $DiSC_{14}(3)$.

Using techniques similar to those used with red blood cells, in vivo lifetime of platelets and distinctions between bleeding or immunologic reaction caused thrombocytopenia are made. Since platelets lack molecules that absorb or emit light in the wavelengths used, however, a wider variety of cyanine dyes are used in making platelet measurements. Such platelet lifetime measurements are used to distinguish post-transfusion bleeding from immunologic reactions, using methodology described above for red blood cells, and in diagnosing atherosclerosis or other diseases in which the effected patient's platelet lifetime differs from that of patients unaffected by the disease. Additionally, the methods described are used to make determinations of in vivo lifetime of other cells, including white blood cells.

In the in vivo cellular tracking analyses, cells are labelled with cyanine dyes that are externally detectable. Such externally detectable dyes include cyanine dyes such as $^{125}$I-labelled DiOC$_{14}$(3). Cell tracking also can be performed using cyanine dyes having a nuclear magnetic reasonance probe thus enabling use of nuclear magnetic reasonance imagery to locate labelled cells. Additionally, fluorescence of the cyanine dyes is used to track cells in areas of the body visible from outside the body. Most commonly, fluorescence is used to track cells in the macula, retina, and blood vessels of the eye. As described in the examples which follow, are uses for in vivo cell tracking which include detection of primary malignancies and metastatic malignant cells, detection of sites of infection, imaging arterial constrictions, and determination of transplant rejection.

The following examples illustrate the present invention and are not intended to limit the scope of the invention as defined above and claimed below.

EXAMPLE 1

Method for Staining Tissue Culture Cells

I. Preparation of Cells

Log phase tissue culture cells are used to obtain best results. Suspension cultures are removed from the culture vessel and placed into polypropylene centrifuge tubes.

When using monolayer cultures, supernatants must be removed and the adherent cells washed with calcium and magnesium free phosphate buffered saline solution to remove serum proteins from the flask. Trypsin-EDTA solution (Gibco Laboratories, Grand Island, N.Y., #610-5300) is added to cover the bottom of the flask and is allowed to incubate at room temperature until the cell monolayer is dislodged and disaggregated. The resultant cell suspension is transferred to a poylpropylene centrifuge tube and an equal volume of culture media containing 10% Fetal Bovine Serum (FBS) (Hazelton) is added to arrest the enzymatic action of the trypsin. Cells are centrifuged at 400×g for ten minutes at room temperature. Supernatants are aspirated and an equal volume of iso-osmotic mannitol is replaced for resuspension of the cell pellet. This mannitol wash is to remove the plasma proteins from the cell suspension and prepare cells for staining. Cells are once again centrifuged at 400×g for ten minutes at room temperature. The supernatants are aspirated and the resultant cell pellet is resuspended in mannitol solution at a concentration of $2 \times 10^6$ cells/ml for staining. Some cell lines, however, are sensitive to the use of a sugar alcohol (mannitol); in such cases an iso-osmotic glucose solution (MW 180.16, 54.05 g/l may be used.

II. Preparation of Stock Dye Solutions $2 \times 10^{-3}$M stock solutions are prepared as follows in absolute ethanol.

| DiO-C$_{14}$(3) | MW 800 (1.600 mg/ml) |
| DiS-C$_{14}$(5) | MW 814 (1.628 mg/ml) |
| DiO-C$_{18}$(3) | MW 936 (1.872 mg/ml) |
| DiI-C$_{14}$(5) | MW 850 (1.700 mg/ml) |

All dyes are obtained from Molecular Probes, Eugene, Oregon.

Dye stocks are sonicated to insure complete solubility of the dye and to minimize adherence to the tubes. Polystyrene tubes are used for preparation of stock solutions so that solubility of the dye can be observed. Polypropylene tubes, however, are used to stain cells because cyanine dyes in an aqueous environment are much less adherent to polypropylene when compared to polystyrene.

III. Cell Staining

Cells are adjusted to a concentration of $2 \times 10^6$ cells/ml in iso-osmotic mannitol. To stain cells, $2 \times 10^{-3}$M stock dye solution is added to the staining solutions at 5 $\mu$l of dye per 1 ml of cell suspension. The sample for staining is pipetted or vortexed to thoroughly mix the sample. Cells are incubated with the dye for ten minutes, after which a small aliquot is removed for examination under a fluorescent microscope to insure that intense and uniform staining has occurred. The DiO dye series uses microscope filters selective for 488 nm excitation light, while the DiS and DiI dye series requires excitation near 575 nm for observation of fluorescence.

After the incubation period, an equal volume of PBS is added to the stain-cell suspension. The cells are centrifuged at 400×g for ten minutes at 20° C. The supernatant is aspirated and the pellet is resuspended in PBS. The centrifugation procedure is repeated and the resultant supernatant is observed for the presence of dye. If dye is apparent in the supernatant, washing is repeated until the supernatants are devoid of free dye as measured by spectrofluorometry. After the final wash, the supernatant is removed and the pellet resuspended to the desired concentration in a suitable culture medium. All procedures are performed under sterile conditions.

EXAMPLE 2

Red Blood Cell Staining

I. Reagent Preparation

A. Citrate Anticoagulant

| 1.66 g | NaCitrate |
| 0.206 g | Citric Acid |
| 0.140 g | NaH$_2$PO$_4$ |
| 1.61 g | Glucose |

The listed components are dissolved in 63 ml of distilled water and the solution is adjusted to a pH of 5.6. The final solution is passed through a 0.22 micron filter for sterilization.

B. Iso-osmotic Glucose Solution

Glucose (54.05 g) is dissolved in one liter of distilled water. The osmolarity is checked using a Fiske osmometer and adjusted to 320 mOsm if necessary.

II. Preparation of Stock Dye

A stock solution of $2 \times 10^{-3}$M DiIC$_{14}$(5) is prepared by dissolving 1.628 mg/ml of dye in absolute ethanol. Sonication may be required to completely solubilize the dye.

III. Staining Procedure

Whole blood is collected aseptically using vacutainers containing sodium citrate or a syringe containing prepared citrate anticoagulant in an amount equal to one tenth the total volume of the syringe. A small aliquot is reserved for flow cytometry or functionality testing. The blood is centrifuged at $100 \times g$ for ten minutes at room temperature to pellet red cells. The plasma containing platelets is removed and reserved, and the red cells are washed by adding iso-osmotic glucose in an amount equal to five times the volume of the packed red cell pellet. The cells should again be centrifuged at $100 \times g$ for ten minutes at room temperature and the supernatant aspirated. This wash which removes the plasma proteins and allows for more intense and uniform staining is repeated one more time. After the final centrifugation and aspiration of the supernatant, the red cells are resuspended in iso-osmotic glucose to a concentration of $4 \times 10^8$ cells/ml.

Prior to the addition of dye, the sample is pipetted or vortexed to insure that sedimentation has not occurred. Fifteen microliters of stock DiSC$_{14}$(5) (2 mM in ETOH) is added to each one milliliter of the red cell suspension. The sample is immediately mixed to insure rapid and uniform distribution of the dye in solution. After approximately five minutes a small aliquot is removed for microscopic observation. A ring is drawn on a glass microscope slide using a wax pencil and a small sample of the cells in staining solution is placed within the wax ring. A coverslip is placed on the slide and the sample is observed. The use of the wax ring lessens discocyte-echinocyte transformation due to the glass slide and coverslip. Use of plastic slides and coverslips will also prevent this transformation. In this way one can insure that the red cell structure is maintained throughout the staining procedure while insuring that intense and uniform staining has occurred. Cells should be uniformly stained after five minutes and exposure times of longer than ten minutes should not be necessary.

After it has been determined that the cells are uniformly stained, an equal volume of phosphate buffered saline is added to the staining suspension. Cells are centrifuged at $400 \times g$ for ten minutes at room temperature, and the supernatant is removed. There will usually be traces of free dye visibly present in the supernatants after centrifugation and therefore the washing procedure using phosphate buffered saline containing calcium and magnesium must be repeated until the supernatants are devoid of free dye as measured by spectrofluorometry.

At this point cells may be either suspended in an appropriate solution for experimentation or platelet poor plasma for reinjection into a recipient animal. For reinjection the general method is to resuspend the stained red cells in the volume of plasma which was recovered from the first centrifugation of the collected whole blood and which has been centrifuged at $4000 \times g$ to remove platelets. All procedures are performed using sterile techniques.

EXAMPLE 3

Staining of Platelets

I. Preparation of Cells

Whole blood is collected in vaccutainers containing sodium citrate or in syringes containing prepared sodium citrate anticoagulant in an amount equal to one tenth the total volume of the syringe. The cells are centrifuged at $100 \times g$ for ten minutes at room temperature to obtain platelet rich plasma. Plastic pipets and polypropylene centrifuge tubes are used for all procedures involving platelets to prevent activation.

The platelet rich plasma is aspirated and transferred to another centrifuge tube. The platelets are then pelleted through the plasma by centrifuging at $1000 \times g$ for ten minutes at $20°$ C. The plasma is then collected and reserved for either functionality testing or use as a suspension medium for reinjection. This plasma should be spun $4000 \times g$ for ten minutes to insure that any residual platelets are removed before use as a resuspension medium, and is referred to as platelet poor plasma (PPP).

The platelet pellet obtained from centrifugation at $1000 \times g$, should be resuspended gently in a small volume of citrate anticoagulant to obtain a concentrated uniform suspension. After this is achieved iso-osmotic glucose may then be added as a diluent, in an amount equal to the plasma originally present. The platelets are then centrifuged at $300 \times g$ for five minutes and the supernatants are aspirated. This glucose wash removes residual plasma proteins and allows for uniform and more intense staining. The platelet pellet is resuspended in the glucose solution and is now ready for staining.

Platelet concentration is adjusted $4 \times 10^8$ cells/ml and 15 $\mu$l of stock DiOC$_{14}$(3) (2 mM in absolute ETOH) is added per ml of platelet suspension. The suspension is immediately but gently and thoroughly mixed to insure even distribution of the dye. Platelets are observed using a fluorescent microscope to insure that uniform staining has occurred and if so are now ready for separation from the free dye in suspension.

II. Use of Sephadex G-100 Column for Separation of Labelled Platelets

Sepharose 2B has been traditionally used to isolate platelets from platelet rich plasma. We have found that Sephadex G-100 also works well in the isolation of platelets. This technique is applied with the staining technology and works in the following manner. A platelet-dye suspension is loaded onto the column. The small molecular weight dye molecules become trapped within the particles while the large platelets are passed directly through the column. In this manner, Sephadex G-100 can be used to separate fluorescently labelled platelets from free dye in suspension.

A. Preparation of Column

Sephadex G-100 (Pharmacia Laboratories, Piscatawav, New Jersey) is hydrated according to the manufacturer's directions, and washed in acetone (100%) in preparation for use as a separation medium for platelets. The washing procedure is carried out by centrifuging the Sephadex at $300 \times g$ for ten minutes at room temperature, removing the supernatant and resuspending in Hanks Balanced Salt Solution. The Sephadex should be repeatedly washed with Hanks Balanced Salt Solution until the odor of acetone is no longer detected. The resultant solution is degassed by insertion in a boiling water bath or by vacuum.

The Sephadex slurry is then used to pour a column. A 10 cc syringe without plunger is used as the column support. Silicone tubing is attached to the hub of the syringe and a small adjustable tubing clamp is used to regulate fluid flow through the column. Forty seven micron nylon mesh is used as a support at the base of the syringe to retain the Sephadex beads. Conventional glass columns with fritted glass filter supports should be avoided since these may serve to activate platelets. The column is filled with Hanks and small amounts of the Sephadex slurry are added to the column. The clamp is opened enough to allow for a slow but consistent flow. This procedure packs the Sephadex evenly and uniformly and prevents channels or air spaces from forming. The procedure of adding HBSS and Sephadex slurry is repeated until the desired size packed column is obtained. The column should be completely flushed with HBSS (2 void volumes) prior to use.

B. Separation of Platelets

The platelet dye and suspension is layered carefully over the Sephadex. The clamp at the bottom of the column should be opened and the fluid level in the column should be allowed to drop until it reaches the top of the Sephadex fluid. Resume flow to allow the suspension to penetrate the Sephadex. Curtail flow again when level is at the top of Sephadex. Add enough HBSS carefully to the top of the column to create a buffer so that additional HBSS can be added easily without disturbing the Sephadex. Again, resume flow of the column. Using this method allows the platelet suspension to form a tight band in the gel and migrate at a fairly uniform rate throughout the length of the column. In this way a more concentrated platelet eluant is obtained. Continue flow through the column, collecting 0.5 to 1.0 ml fractions. The platelet containing fractions will be visible by their opacity and may be pooled together. The pooled fractions are then centrifuged at $300 \times g$ for ten minutes. The supernatant is aspirated and the pellet may be resuspended in a suitable media for experimentation or analysis, or platelet poor plasma supernatant is used for functionality determinations or reinjection.

EXAMPLE 4

Distinguishing Post-Transfusion Bleeding From Immunologic Reactions

A small number of red blood cells from each unit of blood to be transfused is labelled with a fluorescent form of the labelling molecule prior to infusion. Immediately after surgery and blood transfusion, a small aliquot of venous blood is removed and a determination of the percent labelled (percent fluorescent) cells is made by standard flow cytometry or spectrofluorometry procedures. At periodic intervals after the initial venous tap, additional aliquots of blood are removed and similarly analyzed. If internal bleeding is taking place, the ratio of stained to unstained cells does not change even though the hematocrit is dropping. If the patient is experiencing a post-transfusion reaction, then the stained cells (which are the transfused cells) are preferentially destroyed and the ratio of stained to unstained cells drops. This measurement makes possible discrimination between bleeding and post-transfusion immune reactions.

EXAMPLE 5

Diagnosis of Idiopathic Thrombocytopenia

The methodology is the same as Example 4 with the exception that platelet lifetime and platelet production rates are determined. Thus, the patients own platelets are labelled (see Example 3) prior to infusion. Immediately after infusion of the platelets, a small aliquot of venous blood is removed and a determination of the number of labelled (percent fluorescent) platelets per ml is made by standard flow cytometry or spectrofluorometry procedures. At periodic intervals after the initial venous tap, additional aliquots of blood are removed and analyzed for percent positive fluorescence. Plotting the percentage of stained platelets and unstained platelets as a function of time gives the clinician a measure of the rate of destruction of the labelled platelets and the rate of production of the unstained platelets. The rate of production or destruction of platelets is a dynamic measure of the thrombocytopenic process. In this way, the clinician determines whether the idiopathic thrombocytopenia like syndrome is at the level of platelet production or platelet lifetime.

Transfused platelets also are labelled with these dyes. Furthermore, lifetime measurements of donor platelets are made in the same fashion as described for autologous platelets.

EXAMPLE 6

Diagnosis of Atherosclerosis

Diagnosis of atherosclerosis using this method is based upon the hypothesis that the lifetime of an atherosclerotic's platelets is shorter than the lifetime of normal platelets. A small number of the patient's platelets are labelled (according to the protocol in Example 3) with the fluorescent, NMR, or radio-labelling form of the cell labelling dye.

Platelets labelled (see Example 3 for method) with the fluorescent form of the molecule are reinjected and the lifetime of the platelet is determined by serial venipuncture and determination of the remaining number of labelled platelets as a function of time (see Example 5). Platelet lifetime measurements indicating reduced lifetime are diagnostic for atherosclerosis.

Another diagnostic approach is to use a radioisotopic form of the molecule (gamma emitter) and label patients platelets in vitro (using methods of Example 3). Labelled platelets are reinfused and either the lifetime of the platelet is measured using standard isotope counting methods or the patient is imaged using a standard gamma camera to determine if the labelled platelets are adhering to vessel walls.

EXAMPLE 7

Detection of Primary Tumor or Metastasis

Two different cellular methodologies are used in combination with a gamma emitter or an NMR sensitive form of the molecule. In both methodologies tumor cell-seeking cells are used. One methodology uses activated or non-activated lymphocytes and the other methodology uses monocyte, neutrophil or platelet tracking.

Lymphocytes or NK cells are activated in vitro by known procedures using interleukin-2 or an equivalent molecule. These cells then are labelled with the radioactive or NMR form of the molecule using the methods of Example 1, and reinjected into the patient. The patient then is placed under the appropriate imaging device and lymphocyte homing monitored to locate tumors of unknown origin.

A similar methodology uses monocytes from the patient to be tested instead of lymphocytes. In this approach, monocytes are labelled with human or mouse monoclonal antibody which is tumor type specific so that tumor cell recognition is maintained. Foris, G., et al., *Cell. Immuno.* 78:276-284 (1983). These cells then are labelled with the radio-isotopic or NMR-imaging form of the labelling molecule and reinjected in the patient. Time sequential imaging reveals the homing location of the targeted monocytes.

In another methodology for locating primary tumors or metastasis, monocytes, neutrophils or platelets are labelled as described in Example 3 and used to find tumors or metastasis. Since these cells appear early at the tumor site, imaging the labelled cells enables localization of the tumors.

EXAMPLE 8

Detection of Site of Infection

In this application neutrophils are tracked. Neutrophils from the patient to be tested are removed and labelled with the radio-isotopic or NMR-imaging form of the labelling molecule (the methods of Examples 1 and 2 are used for labelling). These cells then are reinfused and imaging of the neutrophil homing using a gamma camera or Nuclear Magnetic Imaging techniques identifies the site of infection. Sequential images are used for identification of dynamic changes in neutrophil pooling and the monitoring of changes resulting from therapeutic intervention.

EXAMPLE 9

Monitoring of Diabetic Retinopathy by Monitoring Macula Degeneration

A small number of red blood cells (type 0, or autologous cells) is labelled (see Example 2 for methods) with a form of the labelling molecule which is excited with a wavelength of light outside the human visible range (greater than 700 nm). The cells then are injected intravenously into the patient. Using standard fluorescence retinal cameras, serial photographs of the vessels of the retina are taken. The cells carrying fluorescent tracers are excited with the appropriate wavelengths and the fluorescence emitted captured on photographic film. Since the dye is trapped in the red cells and the red cells will not migrate outside the vasculature, the fluorescence images are of retinal vessels only.

In another embodiment, the blood flow rate is measured using a standard dual beam laser excitation device which excites the same cell within a vessel at two different points within that vessel. The distance between the excitation points, however, is fixed. Fluorescence is measured at each excitation point, and the length of time required between the two excitation points is a measure of the flow rate of the cells in the vessel.

Blood vessel integrity and blood flow rates are used to measure macula degeneration. Such a monitor is used to evaluate degree of vision impairment and success of treatment in diabetic patients.

EXAMPLE 10

Detection of Impending Stroke in Patients Immediately After Prior Stroke

Platelets from the patient to be scanned are labelled (see Example 3 for methods) with a form of the labelling molecule which is excited with a wavelength of light outside the human visible range (greater than 700 nm). The labelled cells then are injected intravenously into the patient. A standard focused light source (at excitation wavelength) is directed down to a single blood vessel in the retinal bed. Fluorescence is measured using appropriate standard focusing optics and a photomultiplier. The output of the photomultiplier is digitized and recorded in a computer. The fluorescence intensity is a measure of the number of single, double, triple, etc., platelets found in the vein. Increased aggregation of platelets indicates high risk for second stroke.

EXAMPLE 11

Imaging Arterial Constriction

A radio-isotopic form of the molecule (gamma emitter) is used to label the patient's own platelets in vitro (using methods of Example 3) or red cells (using methods of Example 2.). Labelled cells are infused and the patient is imaged using a standard gamma camera to determine if the lumen of the blood vessel is constricted. The red cell labelling may be done with autologous or type O cells from any donor.

EXAMPLE 12

Diagnosis and Staging of Arthritis

Radio-isotopic or NMR imaging forms of the molecule are used to label (methods of Example 1 or 2) lymphocytes, monocytes, or neutrophils from the patient to be tested. These labelled cells then are reinfused into the patient and pooling observed using standard imaging equipment. In arthritis, monocyte tracking is expected to be more useful, and in Degenerative Joint Disease lymphocyte tracking is expected to be more useful. This permits determination of the number of hot joints and evaluation of effects of therapy on the patient's condition.

EXAMPLE 13

Rapid Determination of Transplant Rejection

Lymphocytes, neutrophils or platelets each play an important part in transplant or organ rejection. Patient cells are removed and labelled (using the methods of Examples 1-3) with the radio-isotopic or NMR imaging form of the molecule. Labelled cells are reinjected and sequential imaging done on the patient. At or prior to the time of impending rejection, there is increased localization of the injected cell type in the transplant which is detected by this methodology.

EXAMPLE 14

Diagnosis of Multiple Sclerosis

This application has the same methodology as Example 13, except that localization of cells in the region of the spinal cord or other regions high in myelin is determined.

EXAMPLE 15

Measuring Red Cell Life Span, Red Cell and Blood Volume

Red cell life span is determined in the same fashion as described above for distinguishing bleeding from post transfusion reaction (Example 4). The only difference is that the patients' own red cells are labelled and reinjected. The number of labelled red cells per milliliter is determined (using flowcytometeric or spectrofluorometric methods) as a function of time after injection to determine the life span of these cells.

Red cell mass and blood volume are determined by staining a known number of red cells (autologous or Type O) with the fluorescent form of the dye. A known number of stained red cells ($10^9$) are injected into the individual at time zero and five minutes later an aliquot of blood is removed. The fraction of cells labelled is determined by flow cytometry or by spectrofluorometry. From this dilution factor and knowledge of the total number of cells per $mm^3$, the red cell mass and blood volume is determined.

The preferred embodiments of the invention are illustrated by the above, however, the invention is not limited to the instructions disclosed herein, and the right to all modifications within the scope of the following claims is reserved.

What is claimed is:

1. A method for tracking cells in vivo in a subject that comprises determining the location of cyanine dye-labelled cells previously administered to the subject.

2. A method of claim 1 wherein the cyanine dye has a nuclear magnetic resonance probe.

3. A method of claim 1 wherein the cyanine dye-labelled cells are tumor cell-seeking so that primary or metastatic tumor cells are detected.

4. A method of claim 3 wherein the cyanine dye-labelled cells are lymphocytes or natural-killer cells.

5. A method of claim 4 wherein the lymphocytes or natural-killer cells are activated prior to administration to the subject.

6. A method of claim 3 wherein the tumor cell-seeking cyanine dye-labelled cells are monocytes.

7. A method of claim 3 wherein the tumor cell-seeking cells are monocytes having tumor specific monoclonal antibodies bound to the monocytes so that tumor cell recognition is maintained.

8. A method of claim 3 wherein the tumor cell-seeking cyanine dye-labelled cells are platelets.

9. A method of claim 3 wherein the tumor cell-seeking cyanine dye-labelled cells are neutrophils.

10. A method of claim 1 wherein the cyanine dye is $DISC_{14}(5)$ or $DIOC_{14}(3)$.

11. A method of claim 10 wherein the cyanine dye is tagged with a gamma emitter.

12. A method of claim 10 wherein the cyanine dye is tagged with a nuclear magnetic resonance probe.

13. A method of claim 1 wherein the cyanine dye-labelled cells specifically interact with an organism infecting the subject so that the infection site is determined.

14. A method of claim 13 wherein the organism is a bacterium or fungus.

15. A method of claim 14 wherein the cyanine dye-labelled cells are neutrophils.

16. A method of claim 1 wherein the cyanine dye-labelled cells are red blood cells.

17. A method of claim 16 wherein the subject's retina is examined for presence of cyanine dye-labelled red blood cells to detect retinopathy or blood vessel degeneration.

18. A method of claim 16 wherein the rate at which the cyanine dye-labelled red blood cells flow through blood vessels is measured.

19. A method of claim 16 wherein the excitation wavelength of the cyanine dye is outside the human visable spectrum.

20. A method of claim 1 wherein the cyanine dye-labelled cells are platelets.

21. A method of claim 20 wherein aggregates of cyanine dye-labelled platelets are detected in retinal blood vessels.

22. A method of claim 1 wherein the cyanine dye-labelled cells are monocytes, neutrophils, lymphocytes, or platelets.

23. A method of claim 22 wherein the cyanine dye is tagged with a gamma emitter.

24. A method of claim 23 wherein the cyanine dye-labelled neutrophils are used to detect the location of infection.

25. A method of claim 23 wherein cyanine dye-labelled cells are used with imaging methods to determine arterial constriction.

26. A method of claim 23 wherein the cyanine dye-labelled cells are used in the staging of arthritis.

27. A method of claim 23 wherein the cyanine dye-labelled cells are use to monitor transplant or organ rejection.

28. A method for determining in vivo cell lifetime in a subject that comprises measuring the rate at which cyanine dye-labelled cells administered to the subject disappear from said subject.

29. A method of claim 28 wherein the cyanine dye-labelled cells are used in the staging of arthritis.

30. A method of claim 28 wherein the cyanine dye-labelled cells are red blood cells.

31. A method of claim 30 wherein the rate of disappearance of the cyanine dye-labelled red blood cells is compared to hematocrit changes to distinguish between bleeding and immunologic reaction to the red blood cells.

32. A method of claim 30 wherein total blood volume is determined by injecting a fixed number of completely labelled cells and measuring the dilution factor after equilibration.

33. A method of claim 30 wherein the cyanine dye-labelled red blood cells are prepared by labelling the subject's cells.

34. A method of claim 30 wherein the cyanine dye-labelled red blood cells are prepared by labelling random donor type O red blood cells.

35. A method of claim 28 wherein the cyanine dye-labelled cells are platelets.

36. A method of claim 35 wherein the rate of disappearance of the cyanine dye-labelled platelets is compared to total platelet counts to distinguish between bleeding or decreased platelet production and immunologic reaction to the platelets.

37. A method of claim 35 where the lifetime of cyanine dye-labelled platelets is determined as a measure of atherosclerosis.

38. A method of claim 28 wherein the cyanine dye is $DiSC_{14}(5)$ or $DiOC_{14}(3)$.

39. A method of claim 38 wherein cyanine dye-labelled platelets are measured intraocularly to detect microemboli.

40. A method for tracking cells in vivo in a subject that comprises:

obtaining cells to be cyanine dye-labelled,
labelling the cells with a cyanine dye,
administering the cyanine dye-labelled cells to the subject, and
detecting the cyanine dye-labelled cells.

* * * * *

UNITED STATES PATENT AND TRADEMARK OFFICE
CERTIFICATE OF CORRECTION

PATENT NO. : 4,762,701

DATED : August 9, 1988

INVENTOR(S) : Paul K. Horan et al.

It is certified that error appears in the above-identified patent and that said Letters Patent is hereby corrected as shown below:

Column 15, Claim 1, line 31, delete "previously"

Column 16, Claim 17, line 3, "retinopathv" should read -- retinopathy --.

Column 16, Claim 21, line 13, "cvanine" should read -- cyanine --.

Signed and Sealed this

Fifteenth Day of August, 1989

Attest:

DONALD J. QUIGG

Attesting Officer

Commissioner of Patents and Trademarks